United States Patent
Gutman et al.

(10) Patent No.: US 7,247,730 B2
(45) Date of Patent: Jul. 24, 2007

(54) PROCESS FOR THE PREPARATION OF DEXMETHYLPHENIDATE HYDROCHLORIDE

(75) Inventors: Arie Gutman, Haifa (IL); Igor Zaltsman, Haifa (IL); Anton Shalimov, Haifa (IL); Maxim Sotrihin, Haifa (IL); Gennady Nisnevich, Haifa (IL); Lev Yudovich, Haifa (IL); Irina Fedotev, Haifa (IL)

(73) Assignee: ISP Investments Inc., Wilmington, DE (US)

( * ) Notice: Subject to any disclaimer, the term of this patent is extended or adjusted under 35 U.S.C. 154(b) by 470 days.

(21) Appl. No.: 10/793,080

(22) Filed: Mar. 4, 2004

(65) Prior Publication Data
US 2004/0180928 A1    Sep. 16, 2004

(51) Int. Cl.
*C07D 211/22* (2006.01)
(52) U.S. Cl. ............... 546/226; 546/183; 546/237
(58) Field of Classification Search ........... 546/183, 546/237, 226
See application file for complete search history.

(56) References Cited
U.S. PATENT DOCUMENTS
6,441,178 B2 * 8/2002 Zavareh et al. ............. 546/238

OTHER PUBLICATIONS
Kitagawa et al. "Derivatized cyclodextrin stationary phase . . . " CA 122:329492 (1995).*

* cited by examiner

*Primary Examiner*—Celia Chang
(74) *Attorney, Agent, or Firm*—William J. Davis; Imre Jim Balogh

(57) ABSTRACT

The present invention provides a new and efficient process for the preparation of the dexmethylphenidate hydrochloride with high optical purity, the process comprising:
(a) reacting a solution of threo-N-Boc-ritalinic acid with (S)-1-phenylethylamine, separating precipitated solid salt of (R,R)-enriched N-Boc-ritalinic acid with (S)-1-phenylethylamnine from the reaction mixture and recrystallizing, reslurring and/or trituring of said salt;
(b) mixing the solid salt of (R,R)-N-Boc-ritalinic acid and (S)-1-phenylethylamine obtained in step (a) with aqueous acid and separating (R,R)-N-Boc-ritalinic acid from the mixture; and
(c) reacting the (R,R)-N-Boc-ritalinic acid prepared in step (b) with hydrogen chloride and methanol to give dexmethylphenidate hydrochloride with optical purity of at least 99% ee.

The present invention further provides salt of (R,R)-N-Boc-ritalinic acid with (S)-1-phenylethylamine as new intermediate in the preparation of dexmethylphenidate hydrochloride.

11 Claims, No Drawings

PROCESS FOR THE PREPARATION OF DEXMETHYLPHENIDATE HYDROCHLORIDE

FIELD OF THE INVENTION

The present invention relates to a process for the preparation of dexmethylphenidate hydrochloride and to novel intermediates used in this process.

LIST OF REFERENCES

The following references are considered to be pertinent for the purpose of understanding the background of the present invention:
J. A. Axten et al., J. Org. Chem., 1998, v. 63, 9628-9 and Supporting Info.;
E. J. Corey and A. M. Felix, J. Am. Chem. Soc., 1965, v. 87, 2518-9;
H. M. Deutsch et al., J. Med. Chem., 1996, v. 39, 1201-9;
Y.-S. Ding et al., Psychopharmacology, 1997, v. 131, 71-8;
R. H. Earle et al., J. Chem. Soc. (C), 1969, 2093-8;
L. Panizzon, Helv. Chim. Acta, 1944, v. 27, 1748-56;
K. Patric et al., J. Labelled Compd. Radiopharm., 1982, v. 19, 485-90;
K. S. Patric et al., J. Pharm. Exp. Therap., 1987, v. 241, 152-8;
M. Prashad et al., Tetrahedron: Asymmetry, 1998, v. 9, 2133-6;
M. Prashad et al., Tetrahedron: Asymmetry, 1999, v. 10, 3479-82;
M. Prashad et al., Organic Process R&D, 2000, v.4, 55-9;
L. Szporny et al., Biochem. Pharmacol., 1961, v. 8, 263-8;
U.S. Pat. No. 2,507,631;
U.S. Pat. No. 2,838,519;
U.S. Pat. No. 2,957,880;
U.S. Pat. No. 5,936,091;
U.S. Pat. No. 5,965,734;
U.S. Pat. No. 6,100,401;
U.S. Pat. No. 6,121,453;
U.S. Pat. No. 6,162,919;
U.S. Pat. No. 6,242,464;
U.S. patent application Ser. No. 2002/0019535
WO 98/25902;
WO 99/36403; and
WO 01/27070.

BACKGROUND OF THE INVENTION

Dexmethylphenidate, also known as d-threo-methylphenidate, (R,R)-methylphenidate or (R,R)-α-phenyl-2-piperidineacetic acid methyl ester, having the formula:

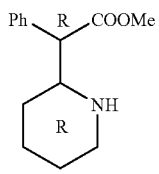

is CNS (central nervous system) stimulant that is chemically and pharmacologically similar to the amphetamines. Dexmethylphenidate's CNS actions is milder than those of the amphetamines and have more noticeable effects on mental activities than on motor activities.

It has been reported by Sporzny (1961) that among racemic mixtures of threo and erythro diastereomers of methylphenidate, only threo-isomer displays stimulant properties. Dexmethylphenidate hydrochloride (i.e. the d-threo enantiomer of methylphenidate hydrochloride) has been reported to be 5 to 38 times more active than the corresponding (S,S)-methylphenidate hydrochloride (Prashad 2000).

A commercially available drug is sold under the name Focalin™ (Novartis) and it consists of dexmethylphenidate in the form of the hydrochloride salt. This product is orally administered and clinically used in the treatment of narcolepsy and as adjunctive treatment in children with attention deficit disorder (ADD) and attention-deficit hyperactivity disorder (ADHD).

A synthesis of dexmethylphenidate hydrochloride was firstly described in U.S. Pat. No. 2,838,519 and include resolution of erythro-α-phenyl-2-piperidineacetamide to obtain enantiopure (2R,2'S)-α-phenyl-2-piperidineacetamide, which was subjected to epimerization, hydrolysis, and esterification as shown in Scheme 1:

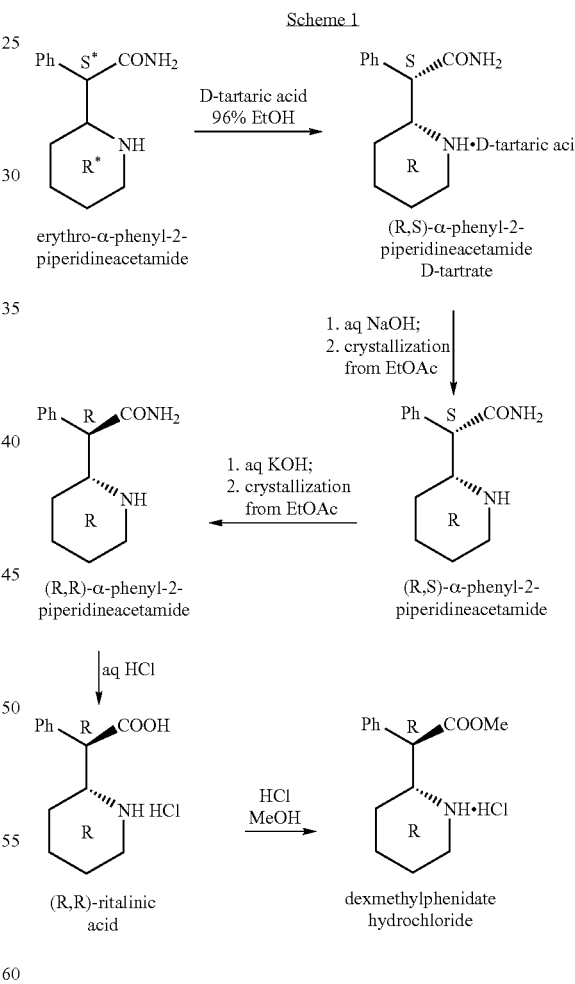

Related example of preparation of dexmethylphenidate from erythro-α-phenyl-2-piperidineacetamide was described in U.S. Pat. No. 5,936,091.

Preparation of dexmethylphenidate through optical resolution of threo-α-phenyl-2-piperidineacetamide was described in U.S. Pat. No. 5,965,734, as shown in Scheme 2:

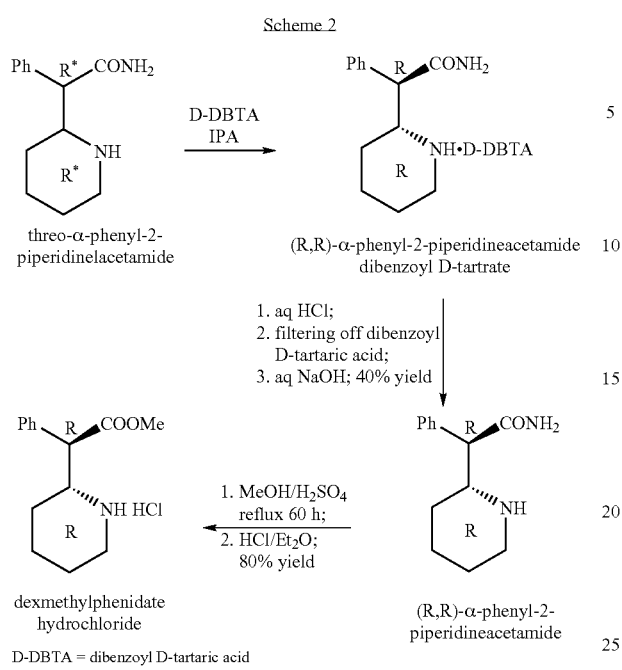

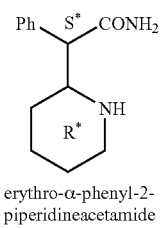

Alternatively, 2-bromopyridine was used instead of 2-chloropyridine by Deutsch (1996).

In some other methods threo-methylphenidate was used as the raw material for the preparation of dexmethylphenidate. Threo-methylphenidate may be prepared by a several routes, inter alia by the following two processes:

i) by esterification of threo-ritalinic acid which may be prepared from erythro-enriched and threo-α-phenyl-2-piperidineacetamides as shown in Scheme 4:

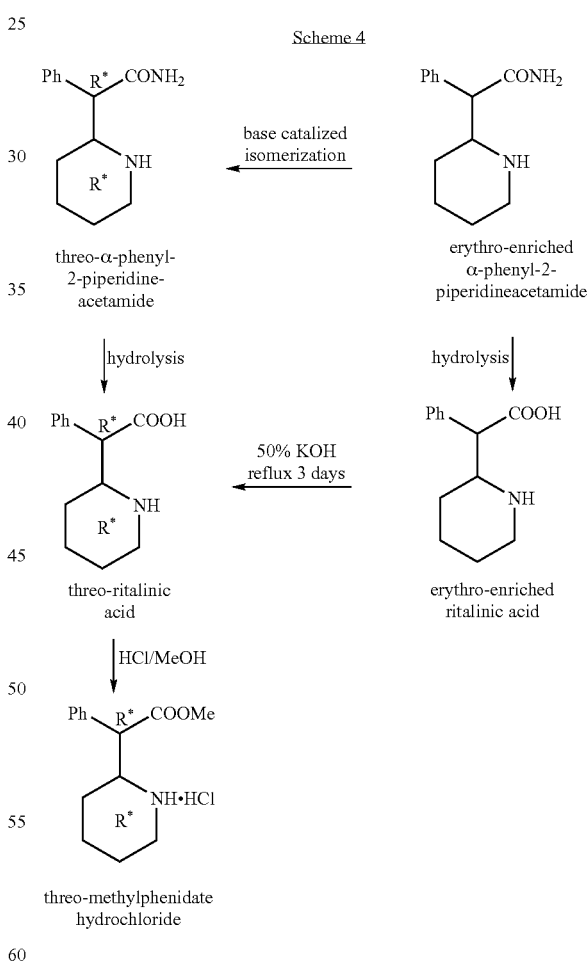

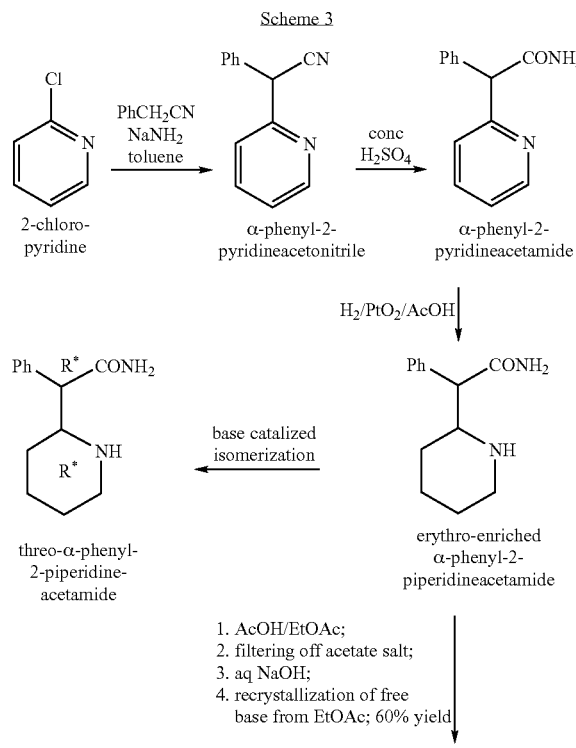

ii) by cyclization of easily available 1-(phenylglyoxylyl) piperidine arenesulfonylhydrazone to (R*,R*)-enriched 7-phenyl-1-azabicyclo[4.2.0]octan-8-one and further converting the β-lactam to threo-methylphenidate hydrochloride, as described by Axten (1998), Corey (1965) and Earle (1969) and in WO 99/36403 and shown in Scheme 5:

Scheme 5

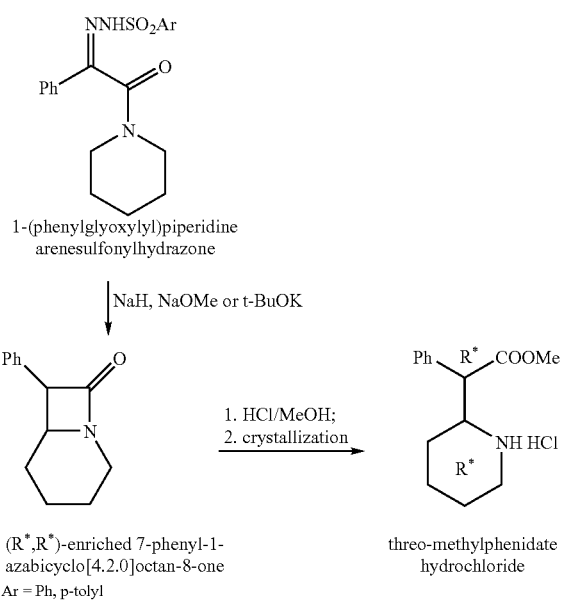

1-(phenylglyoxylyl)piperidine arenesulfonylhydrazone (R*,R*)-enriched 7-phenyl-1-azabicyclo[4.2.0]octan-8-one
Ar = Ph, p-tolyl threo-methylphenidate hydrochloride The resolution of threo-methylphenidate to afford dexmethylphenidate was first reported by Patric (1987) which used (R)-(−)-binaphthyl-2,2'-diyl hydrogen phosphate as the resolving agent. Several new resolutions of threo-methylphenidate have been reported recently by Prashad (1999) and in U.S. Pat. Nos. 6,100,401, 6,121,453, 6,162,919 and 6,242,464 as described in Scheme 6:

Scheme 6

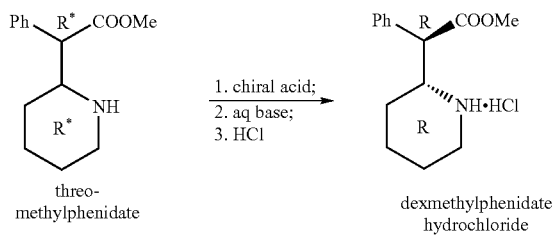

threo-methylphenidate dexmethylphenidate hydrochloride wherein the chiral acid is one of the following: (R)-(−)-binaphthyl-2,2'-diyl hydrogen phosphate, (−)-menthoxyacetic acid, ditoluoyl-D-tartaric acid or dibenzoyl-D-tartaric acid.

Resolution of threo-methylphenidate may be also achieved by enzymatic hydrolysis methods as proposed by Prashad (1998) and in WO 98/25902. Such resolution is described in Scheme 7:

Scheme 7

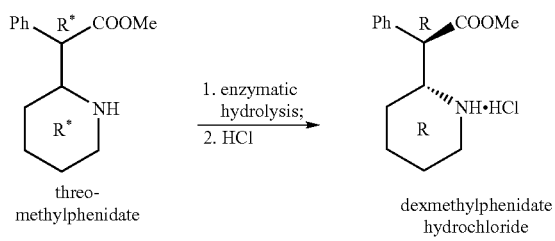

threo-methylphenidate dexmethylphenidate hydrochloride

Resolution of threo-ritalinic acid hydrochloride with (S)-1-phenylethylamine give complex salt (R,R)-enriched threo-ritalinic acid.HCl.(S)-1-phenylethylamine with 77% ee optical purity of ritalinic acid (U.S. Ser. No. 2002/0019535), Scheme 8:

Scheme 8

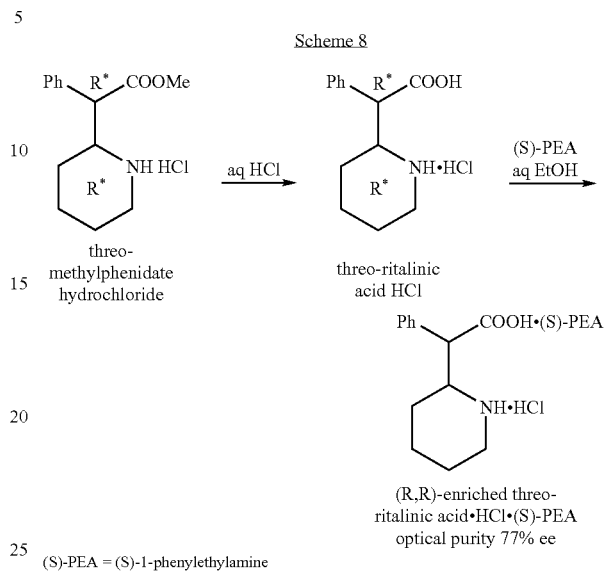

threo-methylphenidate hydrochloride threo-ritalinic acid HCl (R,R)-enriched threo-ritalinic acid·HCl·(S)-PEA
optical purity 77% ee (S)-PEA = (S)-1-phenylethylamine

SUMMARY OF THE INVENTION

It is an object of this invention to provide new and efficient process for the preparation of dexmethylphenidate or its salts, in particular dexmethylphenidate hydrochloride, with high optical purity, which excludes the use of expensive resolving agents.

It is a further object of this invention to provide novel intermediates for the above process.

The above objects are achieved in accordance with the present invention, which in one aspect thereof, provides a process for the preparation of dexmethylphenidate hydrochloride with high optical purity, the process comprising:

(a) reacting a solution of N-protected threo-ritalinic acid with optically active 1-arylethylamine, separating precipitated salt of N-protected (R,R)-enriched ritalinic acid with optically active 1-arylethylamine from the reaction mixture and recrystallizing, reslurring and/or triturating of said salt;

(b) mixing the salt of N-protected (R,R)-ritalinic acid and optically active 1-arylethylamine obtained in step (a) with aqueous acid and separating N-protected (R,R)-ritalinic acid from the mixture; and (c) deprotecting and esterifying the N-protected (R,R)-ritalinic acid prepared in step (b) to give dexmethylphenidate hydrochloride with optical purity of at least 99% ee.

Optical purity is defined by the percent of enantiomeric excess (ee) and in the present case the proportion of the (R,R) isomer in the product is at least 99%. The aryl group of 1-arylethylamine is preferably selected from phenyl, p-tolyl, p-bromophenyl, p-nitrophenyl and naphthyl. More preferably, the resolving agent is (S)-1-phenylethylamine.

Threo-ritalinic acid is preferably N-protected by a group selected from methyl, benzyl, allyl, acyl, alkoxycarbonyl, haloalkoxycarbonyl, arylmethylcarbonyl, allylcarbonyl and vinylcarbonyl. More preferably the N-protecting group is tert-butoxycarbonyl (Boc) group.

In a preferred embodiment, the present invention provides a process for the preparation of dexmethylphenidate hydrochloride having high optical purity, the process comprising:

(i) reacting a solution of threo-N-Boc-ritalinic acid with (S)-1-phenylethylamine, separating precipitated salt of (R,R)-enriched N-Boc-ritalinic acid with (S)-1-phenylethylamine from the reaction mixture and recrystallizing, reslurring and/or triturating of said salt in crystalline form;

(ii) mixing the solid salt of (R,R)-N-Boc-ritalinic acid and (S)-1-phenylethylamine obtained in step (ii) with aqueous acid and separating (R,R)-N-Boc-ritalinic acid from the mixture; and (iii) deprotecting and esterifying the (R,R)-N-Boc-ritalinic acid prepared in step (ii) to give dexmethylphenidate hydrochloride with optical purity of at least 99% ee.

Threo-N-Boc-ritalinic acid is prepared by a process comprising:

(1) contacting a solution of 1-(phenylglyoxylyl)piperidine arenesulfonylhydrazone of the formula

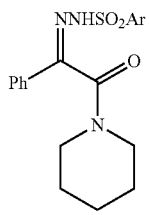

wherein Ar is an aryl group, in a water immiscible organic solvent, with an inorganic base, in the presence of phase transfer catalyst to obtain 7-phenyl-1-azabicyclo[4.2.0]octan-8-one;

(2) reacting the 7-phenyl-1-azabicyclo[4.2.0]octan-8-one of the formula

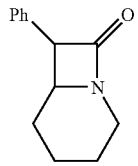

obtained in step (1) with a solution of hydrogen chloride in methanol to give methylphenidate;

(3) reacting the methylphenidate prepared in step (2) with di-tert-butyl dicarbonate to give N-Boc-methylphenidate;

(4) reacting N-Boc-methylphenidate with sodium hydroxide in an alcohol solution or aqueous alcohol solution and separating precipitated solid sodium salt of threo-N-Boc-ritalinic acid from the reaction mixture;

(5) mixing the salt obtained in step (4) with an aqueous acid and separating threo-N-Boc-ritalinic acid from the obtained mixture.

The above process is more efficient if a recycling procedure is carried out after step (4) and before step (5). Such procedure includes:

(ai) acidifying the mother liquor of step (4) and isolating erythro-enriched N-Boc-ritalinic acid from the obtained mixture;

(aii) esterifying of the erythro-enriched acid obtained in step (ai);

(aiii) recycling the N-Boc-methylphenidate obtained in step (aiii) to act as the starting material for step (4).

In accordance with a further aspect of this invention there is provided a novel compound which are salts of (R,R)-N-Boc-ritalinic acid with (S)-1-phenylethylamine and sodium threo-N-Boc-ritalinate. The novel intermediates of the present invention are a stable solid compounds, obtainable in high yield, which can be easily purified by re-crystallizing, reslurrig or triturating and stored for long periods of time.

DETAILED DESCRIPTION OF THE INVENTION

The benefit of the process of the present invention is, inter alia, a process for the optical resolution of racemic N-protected threo-ritalinic acid. According to a preferred embodiment of the invention the process is carried out using optically active 1-arylethylamine as resolving agent.

The process for preparing dexmethylphenidate hydrochloride according to the present invention is schematically shown in Scheme 9 below, starting with threo-N-Boc-ritalinic acid:

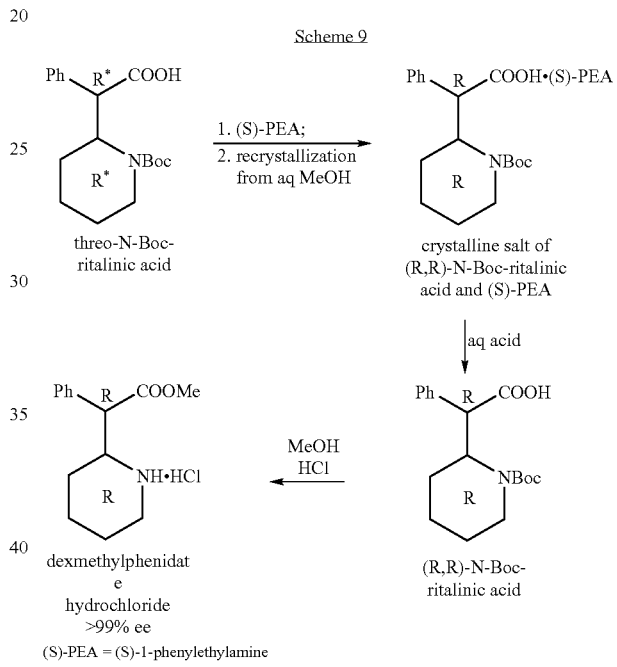

A solution of threo-N-Boc-ritalinic acid is reacted with a resolving agent, e.g. with (S)-1-phenylethylamine, and the salt of (R,R)-N-enriched-Boc-ritalinic acid with (S)-1-phenylethylamine is separated in solid form from the reaction mixture. The purification of the salt includes recrystallizing, reslurring and/or triturating procedures to give the salt of (R,R)-N-Boc-ritalinic acid with (S)-1-phenylethylamine. Upon acidification, (R,R)-N-Boc-ritalinic acid is formed and separated. The reaction of (R,R)-N-Boc-ritalinic acid with hydrogen chloride and methanol gives pure dexmethylphenidate hydrochloride in crystalline form.

N-Protected threo-ritalinic acid may be prepared by N-protecting and hydrolyzing of threo-methylphenidate. For example, N-Boc-threo-ritalinic acid may be prepared by reacting threo-methylphenidate with di-tert-butyl dicarbonate and following hydrolyzing the ester group of obtained N-Boc-threo-methylphenidate.

Preferably threo-N-Boc-ritalinic acid can be prepared by a process comprising:

(i) contacting a solution of 1-(phenylglyoxylyl)piperidine arenesulfonylhydrazone in a water immiscible organic solvent with an inorganic base, in the presence of phase transfer catalyst to obtain 7-phenyl-1-azabicyclo[4.2.0]octan-8-one;

(ii) reacting the 7-phenyl-1-azabicyclo[4.2.0]octan-8-one obtained in step (i) with a solution of hydrogen chloride in methanol to give methylphenidate;

(iii) reacting the methylphenidate prepared in step (ii) with di-tert-butyl dicarbonate to give N-Boc-methylphenidate;

(iv) reacting N-Boc-methylphenidate with solution of sodium hydroxide and separating precipitated solid sodium salt of N-Boc-threo-ritalinic acid from the reaction mixture;

(v) mixing the salt obtained in step (iv) with an aqueous acid and separating threo-N-Boc-ritalinic acid from the obtained mixture;

The above process for preparing starting material N-Boc-threo-ritalinic acid is schematically shown in Scheme 10 below:

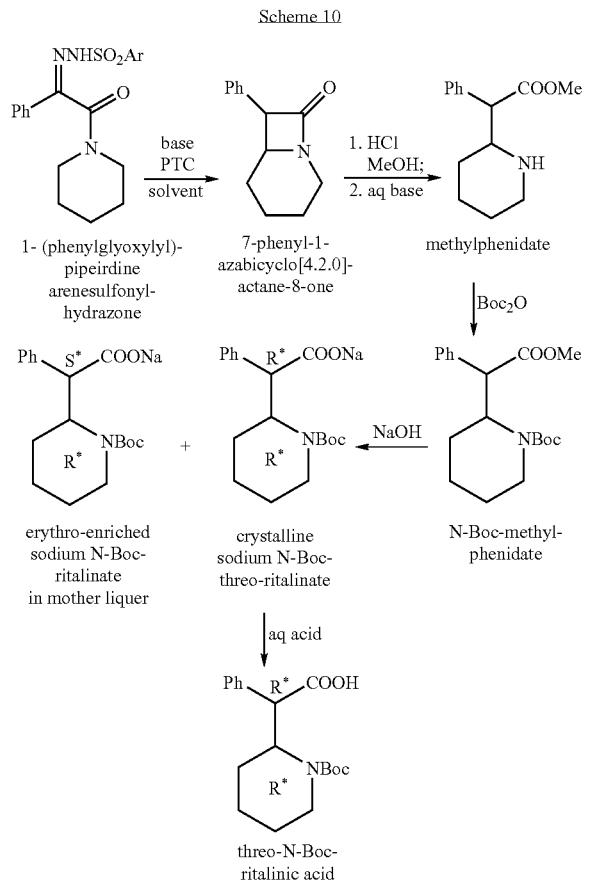

According to a preferred embodiment, the said solution in step (iv) is alcohol or aqueous alcohol solution, wherein the alcohol preferably is methanol, ethanol or isopropanol.

Examples of the aryl group of 1-(phenylglyoxylyl)piperidine arenesulfonylhydrazone are phenyl, p-tolyl, p-chlorophenyl or p-nitrophenyl group. More preferably, 1-(phenylglyoxylyl)piperidine arenesulfonylhydrazone is 1-(phenylglyoxylyl)piperidine p-toluenesulfonylhydrazone.

The phase transfer catalyst is selected from the group consisting of quaternary ammonium and phosphonium salts, polyglycols, crown ethers and podans. Preferably, the phase transfer catalyst is methyltrioctylammonium chloride.

As mentioned above, the reaction is carried out in a water-immiscible organic solvent such as for example halogenated hydrocarbons, e.g. dichloromethane and aromatics, e.g. toluene.

Preferably, the inorganic base is used in solid state or in an aqueous solution and is selected from sodium hydroxide, potassium hydroxide, sodium carbonate or potassium carbonate. More preferably, the said inorganic base is sodium hydroxide.

The present invention further provides sodium salt of N-Boc-threo-ritalinic acid as new intermediate in the preparation of dexmethylphenidate hydrochloride. Sodium N-Boc-threo-ritalinate is stable solid compound which can be easily purified by re-crystallizing, reslurring or triturating and stored for long period of time.

The sodium salt of threo-N-Boc-ritalinic acid precipitates and is separated as a white powder, while the erythro-enriched sodium salt of N-Boc-ritalinate remains dissolved in the mother liquor and may be converted into the threo-isomer and recycled back into the process as the starting material for the second step.

According to a preferred embodiment of the present invention, the process further comprises the recycling of the erythro-enriched N-Boc-ritalinic acid obtained after step (iv) back into step (iv) as a starting material. The following steps constitute the recycling process which is described with reference to the erythro-enriched N-Boc-ritalinic acid:

(ai) acidifying the mother liquor of step (iv) and isolating erythro-enriched N-Boc-ritalinic acid from the obtained mixture;

(aii) esterifying of the erythro-enriched acid obtained in step (ai);

(aiii) recycling the N-Boc-methylphenidate obtained in step (aiii) to act as the starting material for step (iv).

The process for preparing sodium N-Boc-threo-ritalinate from erythro-enriched N-Boc-ritalinic acid sodium salt according to the present invention is schematically shown in Scheme 11 below:

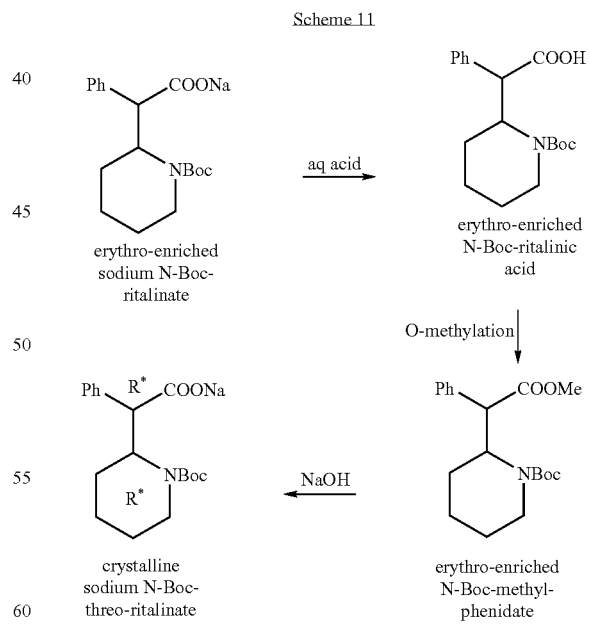

A mixture of about 1:1 threo/erythro-N-Boc-methylphenidate may be prepared by base catalyzed isomerizing of erythro-N-Boc-methylphenidate. Sodium hydroxide play role of strong base and saponifying agent in the conversion of erythro-N-Boc-methylphenidate to sodium threo-N-Boc-ritalinate according to Scheme 12:

Scheme 12

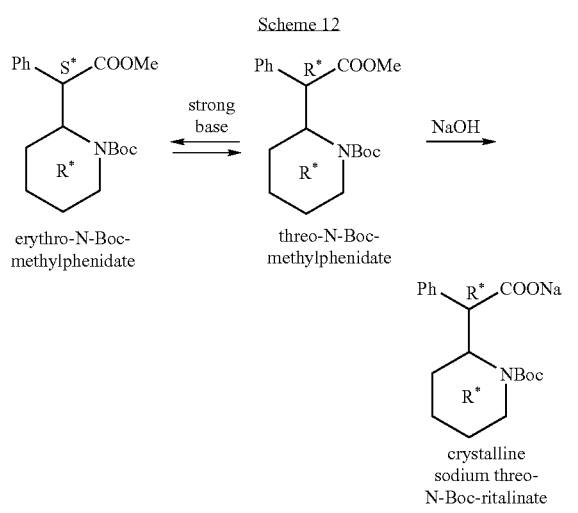

So, erythro-enriched N-Boc-methylphenidate or even erythro-N-Boc-methylphenidate may be used as starting material for preparing dexmethylphenidate according of the process of our invention. erythro-Enriched or erythro-N-Boc-methylphenidate may be obtained by reacting an erythro-enriched or erythro-methylphenidate with di-tert-butyl dicarbonate.

The term "enriched" used in the context of the present invention denotes a higher amount of one entity over others in the mixture. In a similar manner, "threo-enriched" refers to a mixture where the amount of the threo isomer is higher than that of the erythro and "erythro-enriched" refers to a mixture where the amount of the erythro isomer is higher than that of the threo.

The term "substantially pure threo-methylphenidate" relates to a mixture that contains at least 95% of threo-isomer of methylphenidate. By analogy, the term "substantially pure erythro-methylphenidate" describes a mixture that contains at least 95% of erythro-isomer of methylphenidate.

1-(Phenylglyoxylyl)piperidine arenesulfonylhydrazone may be readily prepared by a reaction between 1-(phenylglyoxylyl)piperidine and arenesulfonhydrazide according to Scheme 13:

Scheme 13

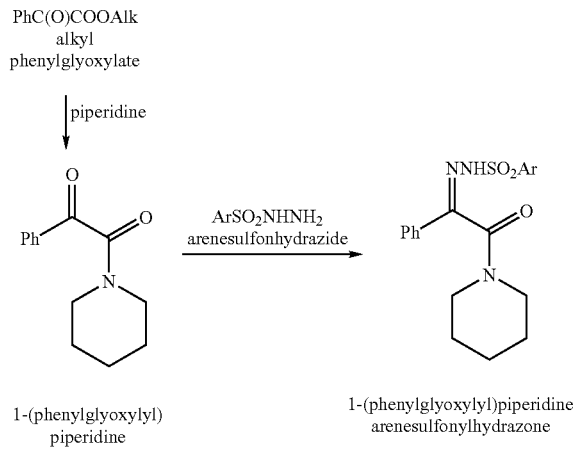

1-(Phenylglyoxylyl)piperidine may be prepared by reaction of alkyl phenylglyoxylate with piperidine. Preferably the alkyl group is methyl or ethyl group.

EXAMPLES

In order to understand the invention and to see how it may be carried out in practice, preferred embodiments will now be described, by way of non-limiting examples only.

Example 1

1-(Phenylglyoxylyl)piperidine

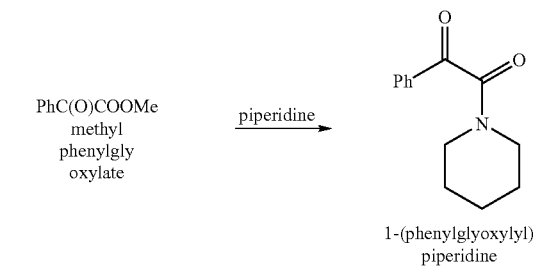

Methyl phenylglyoxylate (12.50 Kg, 76.1 mol, 1 eq) was added dropwise to a stirred mixture of piperidine (19.45 Kg, 228 mol, 3 eq) and methanol (5.0 L) for 3.5 hours to maintain the temperature at 45-55° C. The mixture was stirred at the same temperature for 0.5 hour and kept overnight at +4° C. The precipitated solid was filtered off, washed on the filter with cold methanol (5 L) and dried under reduced pressure to a constant weight to give 15.90 Kg (96%) of 1-(phenylglyoxylyl)piperidine with 99.9% purity by GC.

Example 2

1-(Phenylglyoxylyl)piperidine p-toluenesulfonylhydrazone

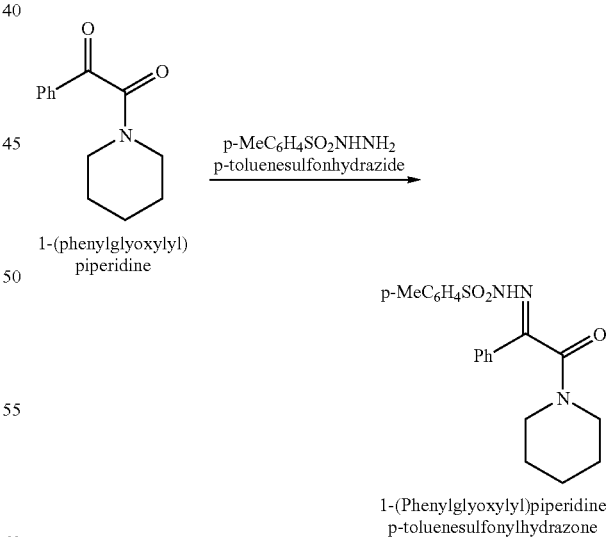

A solution of 98% sulfuric acid (121.7 g, 1.22 mol, 0.02 eq) in abs ethanol (1.0 L) was added dropwise to a stirred mixture of 1-(phenylglyoxylyl)piperidine (17.58 Kg, 80.9 mol, 1 eq), p-toluenesulfonhydrazide (16.20 Kg, 87.0 mol, 1.08 eq) and abs ethanol (50 L) at 20-30° C. The obtained mixture was stirred under reflux conditions until 1-(phenylglyoxylyl)piperidine disappeared (~7 hours, TLC control).

The mixture was stirred for 1 hour at 20-30° C. and kept overnight at 4-6° C. The precipitated solid was filtered off, washed on the filter with cold methanol and cold hexane and dried under reduced pressure to a constant weight to yield 28.25 Kg (90.6%) of 1-(phenylglyoxylyl)piperidine p-toluenesulfonylhydrazone with 99.9% purity by HPLC.

Example 3

7-Phenyl-1-azabicyclo[4.2.0]octan-8-one

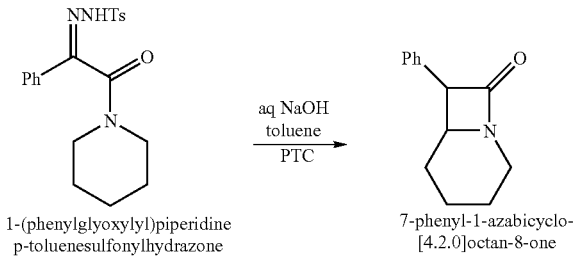

1-(phenylglyoxylyl)piperidine
p-toluenesulfonylhydrazone 7-phenyl-1-azabicyclo-
[4.2.0]octan-8-one Sodium hydroxide, 50% aqueous solution (1.09 Kg, 13.6 mol, 1.05 eq) was added to a stirred mixture of 1-(phenylglyoxylyl)piperidine p-toluenesulfonylhydrazone (5.00 Kg, 13.0 mol, 1 eq), phase transfer catalyst (PTC) trioctylmethylammonium chloride (aliquat 336) (60.0 g, 0.15 mol, 0.01 eq) and toluene (50 L) at 20-30° C. The mixture was heated to reflux and monitored by both TLC and the color of the reaction mixture. The originally yellow solution in 10 minutes turned bright orange as the diazo compound was formed. After 6.5 hours at reflux, the solution re-assumed a yellow color and TLC indicated that no starting material and intermediate were present. Crushed ice (20 Kg) was added to the reaction mixture (temperature of the mixture was dropped to 15° C.). The organic layer was separated, washed with brine (15 L) and evaporated under reduced pressure to give 2.69 Kg (quantitative yield) of 7-phenyl-1-azabicyclo [4.2.0]octan-8-one with R*R*/S*R* 3.3:1 by GC.

Example 4

Methylphenidate

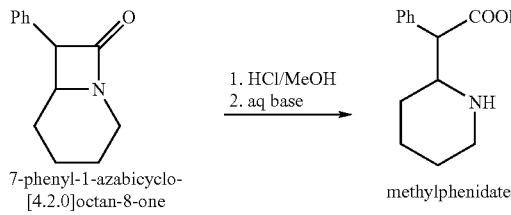

7-phenyl-1-azabicyclo-
[4.2.0]octan-8-one methylphenidate

Hydrogen chloride (gas) was passed through a stirred solution of 7-phenyl-1-azabicyclo[4.2.0]octan-8-one with R*R*/S*R* 3.3:1 by GC (2.61 Kg, 13.0 mol) in methanol (13 L) under reflux conditions for 60 hour until TLC indicated that all starting material had been consumed. The mixture was evaporated under reduced pressure. The residue was treated with hot water (8 L) for 0.5 h. The hot mixture was filtered, cooled to 50° C., washed with toluene (2×1.2 L), cooled to the room temperature, basified with sodium carbonate to pH 10-11 and extracted with dichloromethane (3×2.5 L). The combined organic extracts were dried over sodium sulfate, filtered and evaporated under reduced pressure to give 2.33 Kg (76.9%) of methylphenidate with threo/erythro 3.5:1 by GC.

Example 5

N-Boc-methylphenidate

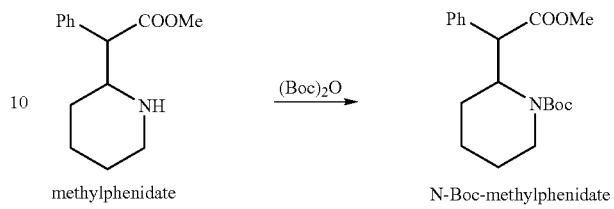

methylphenidate

N-Boc-methylphenidate

A solution of di-tert-butyl dicarbonate (50.5 g, 0.23 mol, 1 eq) in methanol (115 mL) was added dropwise to a stirred solution of methylphenidate with threo/erythro 3.2:1 by GC (54.0 g, 0.23 mol, 1 eq) in methanol (115 mL) with such rate to maintain the temperature at 15-20° C. The mixture was stirred for 6 hours at 20-25° C. (TLC control). Methanol was evaporated from the mixture under reduced pressure. Water (100 mL) and dichloromethane (100 mL) were added to the residue. The aqueous layer was separated and extracted with dichloromethane (3×50 mL). The combined organic layers were dried over sodium sulfate, filtered and evaporated under reduced pressure to give 70.8 g (91.7%) of N-Boc-methylphenidate as off white solidified oil with threolerythro 3.2:1 by HPLC.

Example 6

N-Boc-threo-ritalinic acid sodium salt and erythro-enriched N-Boc-ritalinic acid from threo-enriched methylphenidates

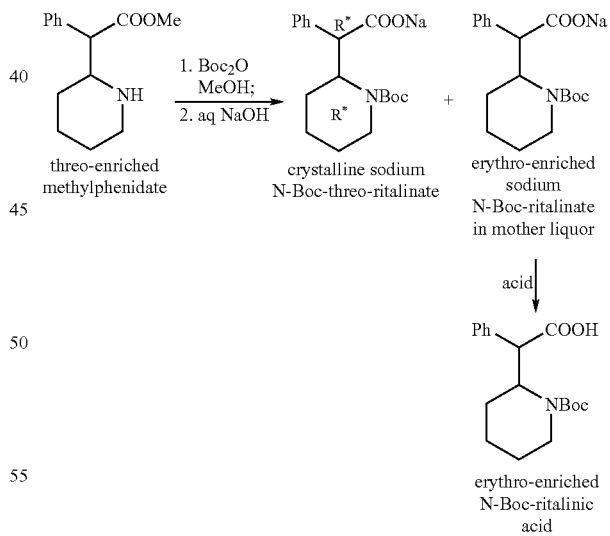

threo-enriched
methylphenidate crystalline sodium
N-Boc-threo-ritalinate erythro-enriched
sodium
N-Boc-ritalinate
in mother liquor erythro-enriched
N-Boc-ritalinic
acid A solution of di-tert-butyl dicarbonate (1459 g, 6.69 mol, 1.0 eq) in methanol (3.3 L) was added dropwise (3.5 h) to a stirred solution of methylphenidate with threo/erythro 4:1 by GC (1560 g, 6.69 mol, 1.0 eq) in methanol (3.3 L) to maintain by cooling ice water the temperature at 10-20° C. The mixture was stirred overnight at 20-25° C. (TLC control). A solution of sodium hydroxide (374.4 g, 9.36 mol, 1.4 eq) in water (3.3 L) was added to the mixture in one portion. The obtained mixture stirred under reflux conditions for 9 hours (TLC control). Methanol was evaporated from the mixture under reduced pressure. Water (2.7 L) was added to the stirred residue. The obtained mixture was kept overnight at 4° C. Precipitated solid was filtered off (Note 1), washed on the filter with ice water (3×1 L) and hexane (2×0.5 L) and dried azeotropicaly with toluene under reduced pressure to a constant weight to give 1700 g (74.5% yield) of N-Boc-threo-ritalinic acid sodium salt as white powder with threo/erythro 97.5:0.5 by HPLC.

Note:

The mother liquor was acidified by 20% aqueous citric acid to pH 4 and thoroughly extracted with ethyl acetate (3×1 L), combined organic extracts were washed with brine (2×0.5 L), dried over sodium sulfate, filtered and evaporated under reduced pressure to constant weight to give 455 g (21.4% yield) of N-Boc-ritalinic acid as off white solidified oil with threo/erythro 5.5/94.5 by HPLC. Analytical sample of N-Boc-erythro-ritalinic acid with mp 170-172° C. was prepared by crystallization of the erythro-enriched N-Boc-ritalinic acid from EtOAc/hexane.

Example 7

N-Boc-threo-ritalinic acid

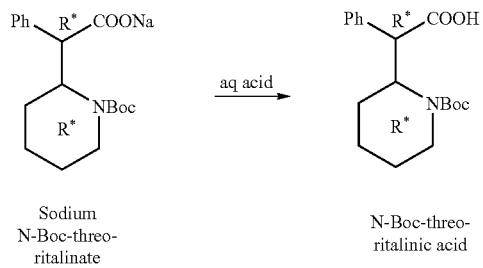

Sodium N-Boc-threo-ritalinate → N-Boc-threo-ritalinic acid

A mixture of solution of N-Boc-threo-ritalinic acid sodium salt (1700 g, 4.98 mmol), citric acid (1150 g, 5.98 mmol) and water (5 mL) was stirred at 15-25° C. for 0.5 hour and extracted with ethyl acetate (3×4 L). Combined organic extracts were washed with brine (2×3 L), dried over sodium sulfate, filtered and evaporated under reduced pressure to constant weight to give 1560 g (98.1% yield) of N-Boc-threo-ritalinic acid with mp 133-134° C. (EtOAc/hexane) and 99.8% purity by HPLC.

Example 8

Salt of (R,R)-N-Boc-ritalinic acid and (S)-1-phenylamine ((S)-PEA)

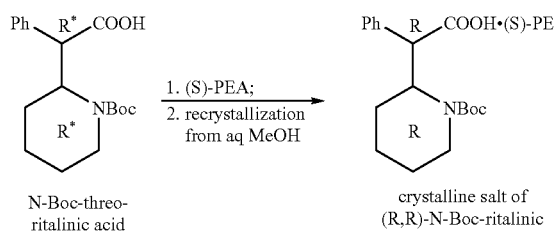

N-Boc-threo-ritalinic acid → crystalline salt of (R,R)-N-Boc-ritalinic acid and (S)-PEA (S)-1-Phenylethylamine (113.8 g, 0.94 mol, 0.6 eq) was added dropwise to a stirred solution of N-Boc-threo-ritalinic acid (500 g, 1.57 mol, 1 eq) in ethyl acetate (5 L) for 1 hour at 20-40° C. The mixture was stirred for 1 hour at 40° C. and overnight at 5° C. The precipitated solids were filtered off, washed on the filter with cold ethyl acetate (2×500 mL) and dried under reduced pressure to give 380 g of white crystals with $[\alpha]_D^{20}$ –23.3° (c=1, MeOH). The salt was twice recrystallized from aqueous methanol. The precipitated crystals were filtered off, washed on the filter with cold aqueous methanol and dried under reduced pressure to a constant weight to give 265 g (33.5% yield) of salt of (R,R)-N-Boc-ritalinic acid and (S)-1-phenylamine as white crystals with $[\alpha]^{D20}$ –28.60 (c=1, MeOH).

Example 9

(R,R)-N-Boc-ritalinic acid

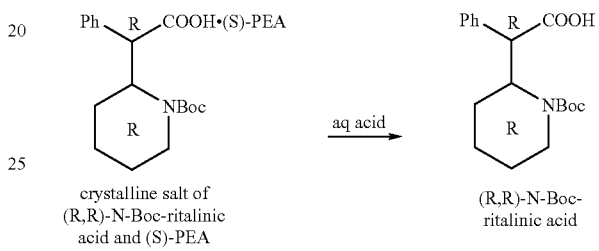

crystalline salt of (R,R)-N-Boc-ritalinic acid and (S)-PEA → (R,R)-N-Boc-ritalinic acid A mixture of crystalline salt of (R,R)-N-Boc-ritalinic acid and (S)-1-phenylamine with $[\alpha]_D^{20}$ –28.6° (c=1, MeOH) (133.0 g, 302 mmol), ethyl acetate (1.3 L) and solution of citric acid (164.0 g, 845 mmol) in water (1.3 L) was stirred at 15-25° C. for 1.5 hours. The organic layer was separated, washed with brine (20 mL), dried over sodium sulfate, filtered and evaporated under reduced pressure to give 95.4 g (99%) of (R,R)-N-Boc-ritalinic acid as white solid with mp 117-119° C. (EtOAc/hexane).

Example 10

Dexmethylphenidate hydrochloride

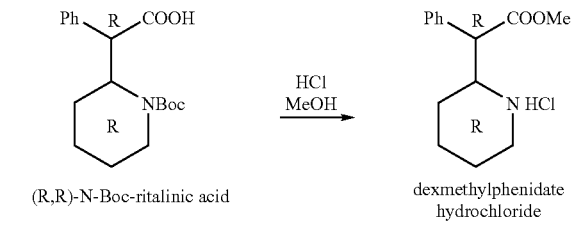

(R,R)-N-Boc-ritalinic acid → dexmethylphenidate hydrochloride

Gaseous hydrogen chloride was passed through a boiling solution of (R,R)-N-Boc-ritalinic acid (95.4 g, 299 mmol) in methanol (1.5 L). The mixture was stirred for 12 hours under reflux conditions and concentrated to the volume of 250 mL. Toluene (750 mL) was added to the stirred residue, then methanol was removed from boiling suspension under normal pressure. The obtained mixture was stirred overnight at 0-5° C. The precipitated solids were filtered off, washed on the filter with toluene (3×50 mL) and dried under reduced pressure to give 78.4 g (97.2% yield) of dexmethylphenidate hydrochloride as white crystals with mp 222-224° C. and $[\alpha]^{D25}$ 87.0° (c=1, MeOH).

Example 11

N-Boc-threo-Methylphenidate

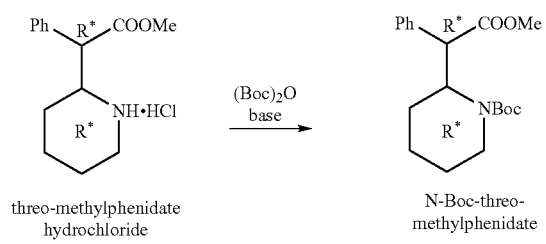

threo-methylphenidate hydrochloride → N-Boc-threo-methylphenidate

A solution of di-tert-butyl dicarbonate (24.0 g, 0.11 mol, 1.1 eq) in dichloromethane (50 mL) was added dropwise to a stirred mixture of threo-methylphenidate hydrochloride (27.0 g, 0.1 mol, 1 eq), dichloromethane (50 mL) and solution of sodium carbonate (10.6 g, 0.1 mol, 2 eq) in water (100 mL) at 0-5° C. The mixture was stirred overnight at a room temperature. The aqueous layer was separated and extracted with dichloromethane (2×50 mL). The combined organic layers were dried over sodium sulfate, filtered and evaporated under reduced pressure. The residue was dissolved in hot hexane (150 mL) and stirred for 1 hour at 0-5° C. The precipitated solids were filtered off, washed on the filter with hexane (30 mL) and dried under reduced pressure to give 27.5 g (82.1%) of N-Boc-threo-methylphenidate with mp 83-84° C.

$^1$H NMR (CDCl$_3$): 7.33 (m, 5H), 4.86 (m, 1H), 4.01 (d, J=12 Hz, 1H), 3.96 (m, 1H), 3.58 (s, 3H), 1.47 (m, 16H)

Example 12

N-Boc-threo-ritalinic acid

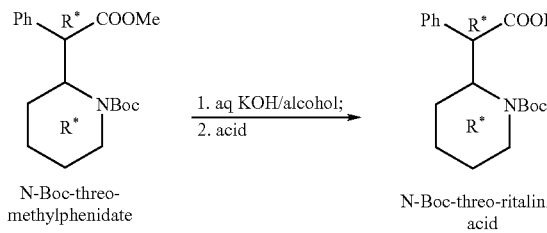

N-Boc-threo-methylphenidate → N-Boc-threo-ritalinic acid

A mixture of N-Boc-threo-methylphenidate (25.0 g, 75.0 mmol, 1 eq), 96% ethanol (50 mL), potassium hydroxide 85% (5.93 g, 90.0 mmol, 1.2 eq) and water (50 mL) was stirred under reflux conditions for 2 hours (TLC monitoring on silica gel, CH$_2$Cl$_2$/MeOH 9:1). Ethanol was evaporated from the mixture. Ethyl acetate (200 mL) and 10% aqueous solution of citric acid (200 g, 104 mmol, 4.2 eq) were added to the stirred resulting aqueous solution of potassium salt at room temperature. The mixture was stirred for 0.5 hour. The organic layer was separated and the aqueous layer was extracted with ethyl acetate (2×100 mL). The combined organic layers were washed with brine (50 mL), dried over sodium sulfate, filtered and evaporated under reduced pressure to give 23.0 g (96% yield) of N-Boc-threo-ritalinic acid.

Example 13

N-Boc-Methylphenidate

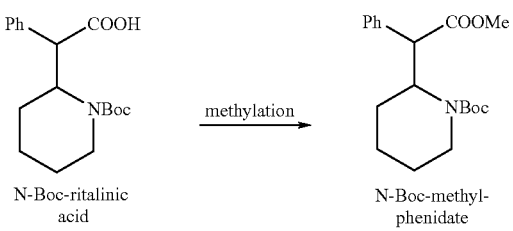

N-Boc-ritalinic acid → N-Boc-methylphenidate

A mixture of N-Boc-ritalinic acid, threo/erythro 5.5:94.5 by HPLC (455.0 g, 1.43 mol, 1 eq), dimethylsulfate (215.6 g, 1.71 mol, 1.2 eq), methyl ethyl ketone (3 L) and potassium carbonate (295.0 g, 2.14 mol, 1.5 eq) was stirred under reflux conditions for 2 hour (TLC control), cooled to 0° C., filtered and washed on the filter with methyl ethyl ketone (3×250 mL). Combined organic filtrates were evaporated under reduced pressure, dissolved in dichloromethane (2.5 L), washed with brine, dried over anhydrous sodium sulfate, filtered off and evaporated under reduced pressure (oil pump) to give 463.0 g (97.5% yield) of N-Boc-methylphenidate with threo/erythro 6.9:93.1 by GC.

Example 14

~1:1 threo/erythro N-Boc-methylphenidate from erythro-enriched N-Boc-methylphenidate

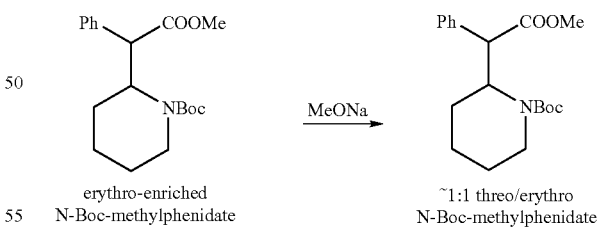

erythro-enriched N-Boc-methylphenidate → ~1:1 threo/erythro N-Boc-methylphenidate A mixture of N-Boc-erythro-methylphenidate with threo/erythro 7:93 (10.0 g, 30.0 mmol, 1 eq), methanol (100 mL) and sodium methoxide (30.0 mmol, 1 eq) was stirred for 3 hours at 20-30° C. and evaporated under reduced pressure. The residue was dissolved in dichloromethane (50 mL), washed with brine, dried over sodium sulfate, filtered, passed through short silica gel column and evaporated under reduced pressure to give 8.9 g (89.0% yield) of N-Boc-methylphenidate with threo/erythro 51.2:48.9 by HPLC.

Example 15

N-Boc-threo-ritalinic acid sodium salt

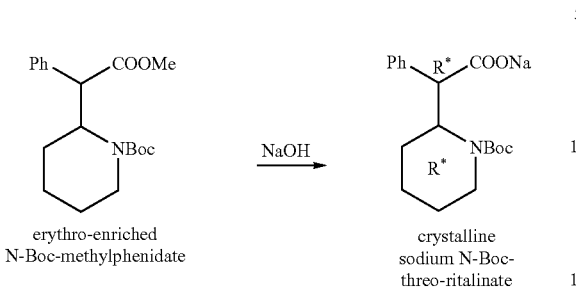

erythro-enriched
N-Boc-methylphenidate crystalline
sodium N-Boc-
threo-ritalinate A mixture of N-Boc-methylphenidate, threo/erythro 7:93 (10.0 g, 30.0 mmol, 1.0 eq), methanol (100 mL) and sodium hydroxide (3.6 g, 90.0 mmol, 3.0 eq) was stirred for 90 hour at 25° C. until the isomerization and hydrolysis had completed (HPLC control). The mixture was evaporated under reduced pressure. A mixture of the residue and water (50 mL) was stirred for 0.5 hour at 60° C., then kept overnight at 5° C. Precipitated solids were filtered off, washed on the filter with cold water (3×10 mL), hexane (2×10 mL) and dried azeotropicaly with toluene under reduced pressure to give 3.2 g (62.7% yield,) of N-Boc-ritalinic acid sodium salt as white powder with threo/erythro 95:5 by HPLC.

The invention claimed is:

1. A process for the preparation of dexmethylphenidate hydrochloride having high optical purity wherein said threo-N-Broc-ritalinic acid is prepared by a process comprising:
   (1) reacting a solution of threo-N-Boc-ritalinic acid with (S)-1-phenylethylamine, separating precipitated salt of (R,R)-enriched N-Boc-ritalinic acid with (S)-1-phenylethylamine from the reaction mixture and recrystallizing, reslurrying and/or triturating of said salt in crystalline form;
   (2) mixing the solid salt of (R,R)-N-Boc-ritalinic acid and (S)-1-phenylethylamine, obtained in step (1) with aqueous acid and separating (R,R)-N-Boc-ritalinic acid from the mixture;
   (3) deprotecting and esterifying the (R,R)-N-Boc-ritalinic acid prepared in step (2) to give dexmethylphenidate hydrochloride with optical purity of at least 99% ee;
   (4) contacting a solution of 1-(phenylglyoxylyl)piperidine arenesulfonylhydrazone of the formula

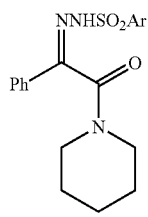

wherein Ar is an aryl group, in a water immiscible organic solvent, with an inorganic base, in the presence of phase transfer catalyst to obtain 7-phenyl-1-azabicyclo[4.2.0]octan-8-one;

(5) reacting the 7-phenyl-1-azabicyclo[4.2.0]octan-8-one of the formula:

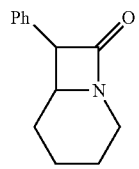

obtained in step (4) with a solution of hydrogen chloride in methanol to give methylphenidate;
   (6) reacting the methylphenidate prepared in step (5) with di-tert-butyl dicarbonate to give N-Boc-methylphenidate;
   (7) reacting N-Boc-methylphenidate with sodium hydroxide in an alcohol solution or aqueous alcohol solution and separating precipitated solid sodium salt of threo-N-Boc-ritalinic acid from the reaction mixture;
   (8) mixing the salt obtained in step (7) with an aqueous acid and separating threo-N-Boc-ritalinic acid from the obtained mixture.

2. The process of claim 1, further comprising the following steps after step (7) and before step (8):
   (i) acidifying the mother liquor of step (4) (7) and isolating erythro-enriched N-Boc-ritalinic acid from the obtained mixtures;
   (ii) esterifying of the erythro-enriched acid obtained in step (i);
   (iii) recycling the N-Boc-methylphenidate obtained in step (ii) to act as the starting material for step (7).

3. The process of claim 1, wherein said alcohol used in step (4) is methanol, ethanol or isopropanol.

4. The process of claim 1, where said phase transfer catalyst is selected from quaternary ammonium and phosphonium salts, polyglycols, crown ethers and podans.

5. The process of claim 1, wherein said phase transfer catalyst is methyltrioctylamminium chloride.

6. The process of claim 1 wherein said water-immiscible organic solvent is dichloromethane or toluene.

7. The process of claim 1 wherein said inorganic base is used in solid state or in an aqueous solution.

8. The process of claim 1 wherein said inorganic base is selected from sodium hydroxide, potassium hydroxide, sodium carbonate and potassium carbonate.

9. The process of claim 1 wherein the aryl group is selected from phenyl, p-tolyl, p-chlorophenyl and p-nitrophenyl.

10. A salt of (R,R)-N-Boc-ritalinic acid with (S)-1-phenylethylamine in a substantially pure solid form of optical purity.

11. Sodium salt of N-Boc-threo-ritalinic acid in a substantially pure solid form of optical purity.

* * * * *